United States Patent [19]
Jeromin et al.

[11] Patent Number: 5,627,289
[45] Date of Patent: May 6, 1997

[54] RECOVERY OF TOCOPHEROL AND STEROL FROM TOCOPHEROL AND STEROL CONTAINING MIXTURES OF FATS AND FAT DERIVATIVES

[75] Inventors: Lutz Jeromin, Hilden; Wilhelm Johannisbauer, Erkrath; Bernhard Gutsche, Hilden; Volkmar Jordan, Mettmann; Herbert Wogatzki, Duesseldorf, all of Germany

[73] Assignee: Henkel Kommanditgesellschaft auf Aktien, Duesseldorf, Germany

[21] Appl. No.: 387,933

[22] PCT Filed: Aug. 18, 1993

[86] PCT No.: PCT/EP93/02207

§ 371 Date: Feb. 27, 1995

§ 102(e) Date: Feb. 27, 1995

[87] PCT Pub. No.: WO94/00650

PCT Pub. Date: May 17, 1994

[30] Foreign Application Priority Data

Aug. 27, 1992 [DE] Germany .................. 42 28 476.7

[51] Int. Cl.⁶ ................................................ C07D 311/72
[52] U.S. Cl. ........................................................ 549/413
[58] Field of Search ................................................ 549/413

[56] References Cited

U.S. PATENT DOCUMENTS

| 3,335,154 | 8/1967 | Smith | 260/345.6 |
| 4,698,186 | 10/1987 | Jeromin et al. | 260/421 |

FOREIGN PATENT DOCUMENTS

| 0171009 | 2/1986 | European Pat. Off. . |
| 0192035 | 8/1986 | European Pat. Off. . |
| 0333472 | 9/1989 | European Pat. Off. . |
| 1170126 | 9/1958 | France . |
| 3126110 | 4/1982 | Germany . |
| 2145079 | 3/1985 | United Kingdom . |
| 2161809 | 1/1986 | United Kingdom . |
| 2218989 | 11/1989 | United Kingdom . |

OTHER PUBLICATIONS

Fat Sci. Technol., vol. 91, @1989, pp. 39 59 41.
Ullmanns Enzyklopädie der technischen Chemie, 4th Edition, vol. 23, @1984, p. 645.

*Primary Examiner*—Johann Richter
*Assistant Examiner*—Laura L. Stockton
*Attorney, Agent, or Firm*—Wayne C. Jaeschke; John Daniel Wood; Daniel S. Ortiz

[57] ABSTRACT

A process is provided for simultaneously recovering tocopherol and sterol from a mixture containing tocopherol, fats and/or fat derivatives, more particularly fatty acids, and sterol and/or sterol derivatives, more particularly from a steamer distillate of natural oils and fats. The steps of said process comprise:

free fatty acids present in the mixture are esterified with a lower alcohol, preferably methanol, 0.4 to 1.6 and more particularly 1 to 1.5 parts by volume of mixture being esterified with 1 part by volume of the lower alcohol, the mixture is subsequently transesterified with the lower alcohol in the presence of a basic catalyst, the excess lower alcohol is distilled off from the reaction mixture after the transesterification, the transesterification catalyst and the glycerol optionally present are removed, more particularly by washing, the fatty acid alkyl ester is distilled off from the mixture, more particularly after removal of the transesterification catalyst, and if desired, tocopherol and sterol are separated by methods known per se. After the transesterification reaction, the alkali catalyst is preferably neutralized with an inorganic acid and the mixture is then washed with water.

12 Claims, No Drawings

RECOVERY OF TOCOPHEROL AND STEROL FROM TOCOPHEROL AND STEROL CONTAINING MIXTURES OF FATS AND FAT DERIVATIVES

This application is a 371 of PCT/EP93/02207 filed Aug. 18, 1993.

BACKGROUND OF THE INVENTION AND FIELD OF THE INVENTION

This invention relates to a process for simultaneously recovering tocopherol and sterol from a mixture containing tocopherol, fats and/or fat derivatives, more particularly fatty acids, and sterol and/or sterol derivatives, more particularly from a steamer distillate of natural oils and fats.

A DISCUSSION OF RELATED ART

Tocopherol compounds occur in many vegetable and animal oils and are also referred to as vitamin E. The vitamin E relates to the physiological effect of these food ingredients.

There are 8 naturally occurring substances with vitamin E activity. They are derivatives of 6-chromanol and belong to two groups of compounds. The first group is derived from tocol and carries a saturated isopren-oidal side chain containing 16 carbon atoms. This group includes alpha-, beta-, gamma- and delta-tocopherol. The compounds differ in their degree of methylation at the benzene ring of the tocol. Alpha-tocopherol is the substance with the strongest biological vitamin E activity and the greatest technical and economical importance. It is the dominant tocopherol in human and animal tissue.

The second group of substances with vitamin E activity are the derivatives of tocotrienol. They differ from the other tocopherol homologs in the unsaturated isoprenoidal side chain containing 16 carbon atoms. The naturally occurring tocoenols also show vitamin E activity and are normally isolated from their natural sources together with the saturated tocopherol homologs in the recovery of vitamin E. In the context of the present invention, the name "tocopherol" is also intended to encompass these tocopherol homologs, i.e. any substances with vitamin E activity.

By virtue of their oxidation-inhibiting properties, the tocopherols are used in foods and in cosmetics and pharmaceuticals and as an additive in paints based on natural oils.

In the context of the invention, the name "sterol" encompasses the sterols which are also known as stearins. The names "sterol" and "stearin" are used synonymously in the present context. The sterols are monohydric secondary steriod alcohols containing 27 to 30 carbon atoms which have the basic structure of gonane. The carbon atom 3 of gonane bears the hydroxyl group. The structural differences between the individual sterols hitherto occurring in nature lie in the presence of double bonds in the ring system, in the appearance of substituents in preferred positions and in the constitution of the side chain which is anchored to carbon atom 17 of gonane.

The most important representative of the sterols is cholesterol which occurs in free or esterified form in animal organs and liquids, particularly in the brain, in the spinal cord, in the suprenal glands, in liver oil and in wool grease. Cholesterol belongs the so-called zoosterols which is the name given to the sterols present in animal fats. Vegetable sterols are called phytosterols. The most important representatives are ergosterol, stigmasterol, campesterol and sitosterol. The stearins or sterols are valuable starting materials in the synthesis of pharmaceuticals, particularly steroid hormones, for example corticosteroids and gestogens. For example, stigmasterol can readily be converted into progesterone.

The starting mixtures for the recovery of tocopherol and sterol may be any of a number of vegetable and animal substances. The highest concentrations of tocopherol are found in vegetable oils, such as wheatgerm oil, corn oil, soybean oil and palm kernel oil. However, tocopherol is also found in other vegetable oils, for example in safflower oil, peanut oil, cottonseed oil, sunflower oil, rapeseed oil, palm oil and other vegetable oils.

The natural plant oils contain only small quantities of tocopherol. Concentration is undesirable for commercial applications. In addition, impurities are supposed to be removed to enhance the antioxidizing effect and vitamin E activity. Accordingly, the most important natural sources of tocopherol are not the vegetable oils themselves, but rather the steam distillates—also known as steamer distillates— obtained in the deodorization of vegetable and animal oils. Although the tocopherols are obtained in concentrated form, they are mixed with sterol and sterol esters, free fatty acids and triglycerides. The distillate from the deodorization of soybean oil is particularly interesting. The particular suitability of soybean oil as a source of tocopherols is mentioned, for example, in Fat Sci. Technol., Vol. 91, 1989, pages 39 to 41 in a comparison of the deodorization distillates of soybean oil and rapeseed oil. The soybean oil steamer distillate contains approximately 10 Ma % mixed tocopherols and the same amount of sterols which are predominantly present in their ester form.

There are various known processes for the concentration of tocopherol, namely esterification, saponification and fractional extraction. Thus, according to DE 31 26 110 A1, tocopherol concentrates are obtained from secondary products of the deodorization of oils and fats by esterification of the free fatty acids present therein by addition of an alcohol or by removal of the free fatty acids from the distillates by distillation, after which these products are subjected to hydrogenation and subsequently to solvent fractionation to extract the tocopherols. Another process for concentrating tocopherol is known from the same document. In this process, the deodorization distillates are subjected to transesterification with methanol and the fatty acid methyl esters are distilled off. The residue is concentrated by molecular distillation.

In another process known from EP 171 009 A2, the tocopherol-containing material is contacted with a sufficient quantity of a polar organic solvent which dissolves the tocopherols, but not the impurities. The polar phase enriched with tocopherol is separated off and the tocopherol is recovered therefrom.

It is also known that the tocopherols can be separated by adsorption onto basic anion exchangers. This variant is possible if the mixture contains little, if any, fatty acid. The sterols, glycerides and other neutral or basic substances are not adsorbed (*Ullmanns Enzyklopädie der technischen Chemie*, 4th Edition, Vol. 23, 1984, page 645).

In one Example, GB 2 145 079 A describes the use of acidic ion exchangers as a catalyst for the esterification of free fatty acids present in rapeseed oil distillate with 5 parts by volume of methanol to 1 part by volume of deodorization distillate. Because constituents insoluble in methanol accumulate, the esterification is carried out in a fluidized bed. The need for the fluidized bed complicates the process and makes it uneconomical to carry out on an industrial scale.

In another process known from EP 333 472 A2 for the production of highly concentrated products containing tocopherol and tocotrienol from palm oil steamer distillate, it is only possible to recover tocopherol and not sterol. This is because reaction times of around 2 hours are required for the transesterification of sterol esters in view of the relatively low reaction rates and are not achieved with the reaction times of 10 minutes sufficient in this process and for the transesterification of glycerides.

It is also known that sterols can be separated from tocopherols by fractional crystallization after concentration. In this process, tocopherol passes into solution and sterol crystallizes out. Tocopherol and sterol can also be separated by distillation, except that in this case the sterol is at least partly destroyed.

Known processes for the recovery of tocopherol and sterol are attended by various disadvantages.

The extraction processes often have to be adapted to the starting mixture because the impurities present therein have a considerable bearing on extraction and the desired useful products, tocopherol and sterol, do not always pass into the desired phase with the same extraction process and different starting mixtures. In addition, known extraction processes use physiologically unsafe solvents.

Ion exchangers have a specific effect on the starting material, require thorough preliminary purification of the mixture and do not allow tocopherol and sterol to be simultaneously concentrated.

In a variant described in DE 31 26 110 A1, tocopherol is subjected to molecular distillation or to steam distillation after esterification of the free fatty acids with polyhydric alcohols in order to obtain a distillate having a high tocopherol content. However, the process step of molecular distillation is uneconomical on an industrial scale while steam distillation involves exposure to relatively high temperatures which at least partly destroys the sterols. In the latter case, therefore, only the thermally more stable tocopherol can be obtained in high yields.

A DESCRIPTION OF THE INVENTION

Accordingly, the problem addressed by the present invention was to provide a process for the simultaneous recovery of tocopherol and sterol which would be applicable to many different starting mixtures and which would not use any toxicologically or ecologically unsafe solvents, would not involve exposure to high temperatures, would give high yields and would be economically workable on an industrial scale.

According to the invention, the solution to this problem is characterized in that 1) free fatty acids present in the mixture are esterified with a lower alcohol, preferably methanol, 0.4 to 1.6 and more particularly 1 to 1.5 parts by volume of mixture being esterified with 1 part by volume of the lower alcohol, 2) the mixture is subsequently transesterified with the lower alcohol in the presence of a basic catalyst, 3) the excess lower alcohol is distilled off from the reaction mixture after the transesterification, 4) the transesterification catalyst and optionally the glycerol present are removed, more particularly by washing, 5) the fatty acid alkyl ester is distilled off from the mixture, more particularly after removal of the transesterification catalyst, and 6) if desired, tocopherol and sterol are separated by methods known per se.

In a first step, the free fatty acids present in the starting mixture are reacted with a lower alcohol to form fatty acid alkyl ester, more particularly fatty acid methyl ester, in order to rule out a saponification reaction with the transesterification catalyst used in the next step. Particularly high reaction rates can be achieved with the above-mentioned range of 1 to 1.5 parts by volume of mixture to lower alcohol. In the case of mixtures with no free fatty acids, this first step may be omitted. In the following process step, transesterification the sterol fatty acid ester is reacted to sterol and fatty acid methyl ester. The partial glycerides and triglycerides react to form glycerol and fatty acid methyl ester. The tocopherol present in the mixture does not react. In many cases, not only tocopherols, but also tocopherol esters are present in the starting mixture, for example in the soybean oil steamer distillate with 0.5 Ma %. In this step, the esters are converted into tocopherols. For the next process step, removal of the excess lower alcohol by distillation, it is of particular advantage if a short-chain alcohol, more particularly methanol, has been used in the preceding steps. In this way, exposure to high temperatures can be minimized. Before removal of the fatty acid alkyl ester by distillation, it is advisable not only to separate the glycerol formed in the transesterification step from triglycerides present, if any, but also to remove the transesterification catalyst. The catalyst is largely present in the form of alkali metal soap which could be problematical during distillation and could lead, for example, to an increase in the boiling point. A highly concentrated tocopherol/sterol mixture is obtained after removal of the fatty acid alkyl ester. The tocopherol and sterol in this mixture can be separated from one another by methods known per se, for example by crystallization.

A major advantage of the process according to the invention is that it can be applied to various mixtures containing tocopherol and, optionally, sterol. In particular, however, it is of advantage to start out from soybean oil steamer distillate which is obtained by steam distillation of crude soybean oil as the first stage of the deodorization process. The distillate contains approximately 20% of sterol, 8% of tocopherol, 20% of free fatty acids and, as its principal constituent, triglycerides (Ullmann, loc. cit.).

However, steamer distillates of other oils, for example rapeseed oil distillates, can also be processed by the process according to the invention.

The process according to the invention is by no means limited in its application to steamer distillates of vegetable oils and fats. It may also be applied with advantage to tall oil. Tall oil is, economically, one of the most important secondary products of the cellulose sulfate process used in papermaking. It is obtained by acidification of the sodium salt mixture of resinic and fatty acids formed in this process. Tall oil is a natural mixture of resinic acids of the abietic acid type, saturated and unsaturated fatty acids and fatty acid esters and an unsaponifiable fraction. In addition to higher alcohols and hydrocarbons, the unsaponifiable fraction also contains sterols.

Other mixtures containing tocopherol may also be worked up by the process according to the invention, for example the residue obtained in the production of rapeseed oil methyl ester which also contains sterols and sterol esters.

In one preferred embodiment of the process according to the invention, the fatty acids are esterified in the presence of a strongly acidic ion exchanger, more particularly present in a fixed-bed reactor, at temperatures in the range from 60° to 100° C. and more particularly at temperatures in the range from 65° to 70° C. The distinctly smaller loss of tocopherol through its solubility in methanol than occurs in the removal of the fatty acids by distillation was both advantageous and surprising. In the esterification of the fatty acids, the ratio of the volume streams between steamer distillate and lower alcohol is between 1.1 and 1.7 and preferably 1.4. The residence time in the fixed-bed reactor is 1 to 2 hours and preferably 1.6 hours. These figures apply to the free volume actually present. In esterification, the fatty acids present in the mixture are reacted to fatty acid alkyl ester at the active centers of the strongly acidic ion exchanger.

After the reaction, the excess lower alcohol, i.e. generally methanol, is removed in a phase separator. The alcohol additionally contains the predominant part of the water formed during the esterification.

After the transesterification and the removal of the excess alcohol from the reaction mixture, the catalyst and any glycerol present are removed from the mixture. The catalyst is preferably neutralized beforehand by acidification with an inorganic acid.

The following Examples are intended to illustrate the invention without limiting it in any way.

EXAMPLES

Example 1

Esterification of the Fatty Acids

Soya steamer distillate having an acid value of 70 was introduced at a volumetric flow rate of 0.094 l/h together with 0.067 l/h methanol into a 0.3 m long glass column charged with catalyst, namely a strongly acidic macroporous ion exchanger resin (Lewatit K 2631). The diameter of the column was 0.07 m. After a residence time of 1.6 h, the mixture was collected in a glass vessel and decanted. Subsequent concentration by evaporation to separate the methanol/water mixture from the fatty phase was carried out in vacuo. The acid value was subsequently determined at 1.3, corresponding to a conversion of 98%, i.e. the loss of tocopherol was negligible. Accordingly, the material has been deacidified for the following transesterification step.

Example 2

Transesterification of the Glycerides and Sterol Esters

The soya steamer distillate deacidified in the first step (acid value approx. 1) was contacted with methanol and the basic catalyst in a tube reactor. The reaction temperature was between 60° and 90° C. and preferably 65° C. Based on the soya steamer distillate used, 40 to 80% of methanol (preferably 50 to 60%) and 0.8 to 1.5% of catalyst (preferably 1%) were used. Sodium methylate was preferably used as the catalyst, although other basic catalysts, for example sodium, potassium and lithium hydroxide, etc., may also be used. The reaction time was approx. 2 h at 65° C. After the transesterification, at least 90% of the sterol esters and at least 95% of the glycerides had been reacted.

Example 3

Transesterification of the Glycerides and Sterol Esters 2.8 kg of deacidified soya steamer distillate, acid value 1.9, were contacted with 1.4 kg of methanol in which 192 g of 30% methanolic sodium methylate had been dissolved. The mixture was heated with continuous stirring to 65° C. and was kept at that temperature for 2 h. To avoid losses of tocopherol, a nitrogen atmosphere was established.

The starting mixture contained approximately 6% of free sterols, a value of 16% being determined after transesterification following removal of the methanol component. The initial glyceride content of 25% fell to 1.2%. 90% of the glycerides were monoglycerides. Triglycerides could no longer be detected.

Example 4

Removal of the Excess Methanol and Separation of Catalyst And Glycerol

After the transesterification, the excess methanol was distilled off from the reaction mixture at a temperature of 90° C./100 mbar.

The demethanolized reaction mixture contained the catalyst used mainly in the form of the alkali metal soap. To remove the catalyst from the steamer distillate, 2.2 kg of demethanolized soya steamer distillate were acidified with 148 g of 3% hydrochloric acid and washed with 1.1 kg of water. Both phases were separated in a decanter.

Example 5

Separation of the Methyl Ester

After distillation of the methyl ester formed from the product of Example 4, a mixture containing 40 Ma % of free sterols and 30 Ma % of tocopherols was obtained.

We claim:

1. A process for the recovery of tocopherol and sterol concentrates from tocopherol- and sterol-containing mixtures of fats and fat derivatives comprising:
   (a) esterifying free fatty acids in said mixture with methanol in the presence of a solid acidic catalyst, to form an esterified mixture containing fatty acid methyl esters;
   (b) separating the solid acidic catalyst from the esterified mixture;
   (c) removing water from the esterified mixture to form a dried esterified mixture;
   (d) transesterifying triglycerides in said dried esterified mixture by alkali-catalyzed transesterification with methanol to form a transesterified mixture;
   (e) removing unreacted methanol from the transesterified mixture to form a demethanolized mixture;
   (f) removing akali catalyst from the demethanolized mixture by acidifying and then washing the demethanolized mixture to form a washed mixture; and
   (g) removing by distillation fatty acid methyl esters from the washed mixture.

2. The process as claimed in claim 1 wherein steamer distillates of soybean oil are used as the mixtures of fats and/or fat derivatives.

3. The process as claimed in claim 1 wherein said acidifying is effective to neutralize the alkali of said alkali-catalyzed transesterification.

4. The process as claimed in claim 1 wherein an inorganic acid is used in said acidifying.

5. The process as claimed in claim 4 wherein said inorganic acid is hydrochloric acid.

6. The process of claim 1 wherein water is used in said washing.

7. The process of claim 1 wherein in said esterifying of said free fatty acids, 0.4 to 1.6parts by volume of mixture is esterified using 1 part by volume of methanol.

8. The process of claim 7 wherein 1 to 1.5 parts by volume of mixture is esterified using 1 part by volume of methanol.

9. The process as claimed in claim 2 wherein said free fatty acids are esterified at temperatures of 60° to 100° C. in the presence of a strongly acidic ion exchanger.

10. The process as claimed in claim 9 wherein said esterifying is carried out in a fixed-bed reactor.

11. The process as claimed in claim 9 wherein said temperatures are 65° to 70° C.

12. A process for the recovery of tocopherol and sterol concentrates from tocopherol and sterol-containing mixtures of fats and fat derivatives comprising:

(a) esterifying free fatty acids in said mixture with methanol, said mixture being a steamer distillate of soybean oil, in the presence of a solid acidic catalyst to form an esterified mixture containing fatty acid methyl esters;

(b) separating the acidic catalyst from the esterified mixtures;

(c) removing water from the esterified mixture to form a dried esterified mixture;

(d) transesterifying triglycerides in said dried esterified mixture by alkali-catalyzed transesterification with methnol to form a transesterified mixture;

(e) removing unreacted methanol from the transesterified mixture to form a demethanolized mixture;

(f) acidifying the demethanolized mixture to neutralize said demethanolized mixture and then washing the demethanolized mixture with water to form a washed mixture; and (g) removing by distillation fatty acid methyl esters from the washed mixture to recover a mixture comprising tocopherol and sterol.

\* \* \* \* \*